(12) United States Patent
Tondokoro et al.

(10) Patent No.: US 9,239,308 B2
(45) Date of Patent: Jan. 19, 2016

(54) HUMIDITY DETECTION SENSOR AND A METHOD FOR MANUFACTURING THE SAME

(71) Applicant: ALPS ELECTRIC CO., LTD., Tokyo (JP)

(72) Inventors: Atsushi Tondokoro, Miyagi-ken (JP); Satoshi Waga, Miyagi-ken (JP); Takashi Sato, Miyagi-ken (JP); Shinya Yokoyama, Miyagi-ken (JP); Sumihito Morita, Miyagi-ken (JP)

(73) Assignee: ALPS ELECTRIC CO., LTD., Tokyo (JP)

( * ) Notice: Subject to any disclaimer, the term of this patent is extended or adjusted under 35 U.S.C. 154(b) by 338 days.

(21) Appl. No.: 13/851,795

(22) Filed: Mar. 27, 2013

(65) Prior Publication Data

US 2013/0207673 A1 Aug. 15, 2013

Related U.S. Application Data

(63) Continuation of application No. PCT/JP2011/068082, filed on Aug. 8, 2011.

(30) Foreign Application Priority Data

Oct. 4, 2010 (JP) ................................. 2010-224660

(51) Int. Cl.
*G01R 27/26* (2006.01)
*G01N 27/22* (2006.01)
(Continued)

(52) U.S. Cl.
CPC ................ *G01N 27/223* (2013.01); *G01N 1/00* (2013.01); *G01N 2201/00* (2013.01); *H01L 21/00* (2013.01); *Y10T 29/49* (2015.01)

(58) Field of Classification Search
CPC . G01N 1/00; G01N 2201/00; G01N 2203/00; H01L 21/00; H01L 2221/00; H01L 2223/00
USPC .......................................................... 324/664
See application file for complete search history.

(56) References Cited

U.S. PATENT DOCUMENTS 4,975,249 A * 12/1990 Elliott ............................. 422/83
6,690,569 B1 2/2004 Mayer et al.
(Continued)

FOREIGN PATENT DOCUMENTS

JP 07-020080 1/1995
JP 10-221288 8/1998
(Continued)

OTHER PUBLICATIONS

International Search Report dated Nov. 15, 2011 from International Application No. PCT/JP2011/068082.

*Primary Examiner* — Huy Q Phan
*Assistant Examiner* — Temilade Rhodes-Vivour
(74) *Attorney, Agent, or Firm* — Beyer Law Group LLP

(57) ABSTRACT

A humidity detection sensor includes a lower electrode provided on a board, an upper electrode provided so as to face the lower electrode, a humidity sensing film which is formed at least between the lower electrode and the upper electrode and whose dielectric constant changes in response to humidity, and a protective film provided so as to cover the upper electrode. Each of the upper electrode and the protective film has an opening through which the humidity sensing film is partially exposed to the outside. In the opening, the humidity sensing film is provided so as to reach at least a position higher than the position of the lower surface of the protective film.

9 Claims, 6 Drawing Sheets

(51) Int. Cl.
  *G01N 1/00* (2006.01)
  *H01L 21/00* (2006.01)

(56) References Cited

U.S. PATENT DOCUMENTS

| | | |
|---|---|---|
| 2002/0136664 A1 | 9/2002 | Lee et al. |
| 2003/0091355 A1* | 5/2003 | Jeschonek ............... G01N 33/32 399/49 |
| 2003/0179805 A1* | 9/2003 | Hamamoto et al. ............ 374/16 |
| 2004/0080325 A1 | 4/2004 | Ogura |
| 2004/0182153 A1* | 9/2004 | Hamamoto ................ 73/335.04 |
| 2006/0186901 A1* | 8/2006 | Itakura ................. G01N 27/223 324/689 |
| 2006/0260107 A1* | 11/2006 | Itakura ................. G01N 27/225 29/25.03 |
| 2007/0273394 A1* | 11/2007 | Tanner ................. A01G 25/167 324/664 |
| 2008/0024110 A1* | 1/2008 | Nikolaus .............. G01N 27/228 324/71.1 |

FOREIGN PATENT DOCUMENTS

| | | |
|---|---|---|
| JP | 2002-243690 | 8/2002 |
| JP | 2003-516538 | 5/2003 |
| JP | 2009-019964 | 1/2009 |
| WO | WO 2010/113711 | 7/2010 |

* cited by examiner

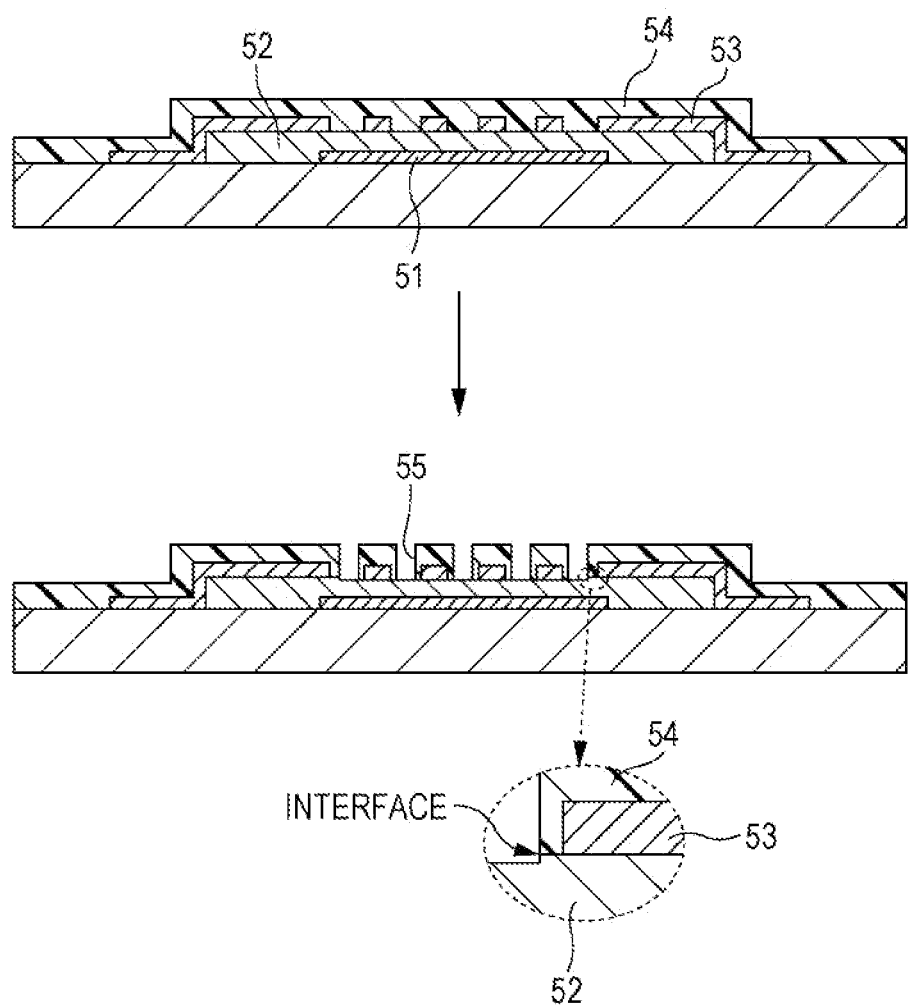

HUMIDITY DETECTION SENSOR AND A METHOD FOR MANUFACTURING THE SAME

CLAIM OF PRIORITY

This application is a Continuation of International Application No. PCT/JP2011/068082 filed on Aug. 8, 2011, which claims benefit of Japanese Patent Application No. 2010-224660 filed on Oct. 4, 2010. The entire contents of each application noted above are hereby incorporated by reference.

BACKGROUND OF THE INVENTION

1. Field of the Invention

The present invention relates to a humidity detection sensor including a dielectric substance as a humidity sensing film and a method for manufacturing the same.

2. Description of the Related Art

As a humidity detection sensor used for measuring a humidity change, there is a capacitance type humidity detection sensor including a dielectric substance as a polymer humidity sensing film whose dielectric constant changes in response to an amount of absorbed or discharged water. The capacitance type humidity detection sensor includes a sensor section whose capacitance changes in response to humidity; and a reference section that keeps its capacitance constant regardless of humidity. The capacitance type humidity detection sensor converts the capacitance difference between the sensor section and the reference section to a voltage and outputs the voltage. Each of the sensor section and the reference section has a lamination structure in which a polymer humidity sensing film is interposed between a pair of electrodes. Such a humidity detection sensor is disclosed, for example, in PCT Japanese Translation Patent Publication No. 2003-516538.

As disclosed in PCT Japanese Translation Patent Publication No. 2003-516538, as the structure of the humidity detection sensor, there is a structure in which a pair of opposed comb electrodes are provided on the same plane and a humidity sensing film is provided on the pair of comb electrodes, or a structure in which a humidity sensing film is provided between a lower electrode formed on a board and an upper electrode provided on the lower electrode so as to face the lower electrode.

The structure in which the humidity sensing film is provided between the upper and lower electrodes is formed by laminating the lower electrode, the humidity sensing film, and the upper electrode in order, and thus it is possible to easily control the thickness and smoothness of the humidity sensing film as compared to the case where the humidity sensing film is provided on the comb electrodes provided on the same plane. Meanwhile, in the case of the parallel-plate structure in which the humidity sensing film is interposed between the upper and lower electrodes, the upper electrode is exposed, and thus a problem of humidity resistance, such as corrosion of the upper electrode due to water or the like, arises.

As a solution to the problem, it is conceivable to form a protective film on the upper electrode of the sensor section. However, as described in PCT Japanese Translation Patent Publication No. 2003-516538, in the parallel-plate structure in which the humidity sensing film is provided between the upper and lower electrodes, when the upper electrode is partially removed to partially expose the humidity sensing film, thereby smoothly supplying water molecules to the humidity sensing film, if a protective film is formed over the entire surface, external water molecules cannot smoothly be supplied to the humidity sensing film. Meanwhile, a method of selectively forming the protective film only on the upper electrode is conceivable. However, in this case, a problem of corrosion from side surfaces of the exposed upper electrode is considered.

SUMMARY OF THE INVENTION

The present invention has been made in view of such a point and provides a humidity detection sensor that has a structure in which a humidity sensing film is interposed between a lower electrode and an upper electrode, that smoothly supplies external water molecules to the humidity sensing film, and that has improved humidity resistance of the upper electrode.

According to the present invention, a humidity detection sensor includes a board; and a sensor section provided on the board, a capacitance of the sensor section changing in response to humidity. The sensor section includes: a lower electrode provided on the board, an upper electrode provided so as to face the lower electrode; a humidity sensing film formed at least between the lower electrode and the upper electrode, a dielectric constant of the humidity sensing film changing in response to the humidity; and a protective film provided so as to cover the upper electrode. Each of the upper electrode and the protective film has an opening through which the humidity sensing film is partially exposed to an outside. In the opening, the humidity sensing film is provided so as to reach at least a position higher than a position of a lower surface of the protective film.

According to this configuration, even when the protective film is provided so as to cover the upper electrode and the opening is provided through which the humidity sensing film is partially exposed, it is possible to provide a configuration in which the interface at which the lower surface of the protective film and the humidity sensing film are in contact with each other is not exposed to the outside. Thus, it is possible to suppress entry of water molecules or a corrosion component through the interface, and hence external water molecules are smoothly supplied to the humidity sensing film and it is possible to effectively improve the humidity resistance of the upper electrode.

In the humidity detection sensor according to the present invention, the humidity sensing film preferably fills the opening and is formed on the protective film.

In the humidity detection sensor according to the present invention, preferably, the opening formed in the upper electrode is larger than the opening formed in the protective film, and the protective film is provided so as to cover a side surface of the upper electrode and be partially in contact with the humidity sensing film.

In the humidity detection sensor according to the present invention, the humidity sensing film is preferably formed from any of polyimide, cellulose, and PVA (polyvinyl alcohol).

Preferably, the humidity detection sensor according to the present invention further includes a reference section provided on the board, the reference section including a pair of electrodes and a humidity sensing film interposed between the electrodes and formed from the same material as that of the humidity sensing film provided in the sensor section, a capacitance of the reference section not changing regardless of the humidity, and a capacitance difference between the sensor section and the reference section is converted to a voltage and the voltage is outputted.

According to the present invention, a method for manufacturing a humidity detection sensor includes the steps of: forming a lower electrode on a board; forming, on the lower electrode, a first humidity sensing film whose dielectric constant changes in response to humidity; forming, on the first humidity sensing film, an upper electrode facing the lower electrode; forming, in the upper electrode, a first opening through which the first humidity sensing film is exposed; forming a protective film on the upper electrode and an exposed portion of the first humidity sensing film; forming, in the protective film, a second opening through which the first humidity sensing film is exposed; and forming a second humidity sensing film in the second opening such that the second humidity sensing film reaches at least a position higher than a position of an interface at which a lower surface of the protective film and an upper surface of the first humidity sensing film are in contact with each other.

In the method for manufacturing the humidity detection sensor according to the present invention, the second humidity sensing film is preferably formed also on the protective film.

In the method for manufacturing the humidity detection sensor according to the present invention, materials of the first humidity sensing film and the second humidity sensing film are preferably the same.

In the method for manufacturing the humidity detection sensor according to the present invention, the second opening is preferably formed so as to be smaller than the first opening.

BRIEF DESCRIPTION OF THE DRAWINGS

FIG. 6 is a diagram illustrating a structure in the case where, when a parallel-plate structure in which a humidity sensing film is interposed between upper and lower electrodes is provided in the sensor section of the humidity detection sensor, a protective film is provided on the upper electrode.

Figure 1A:
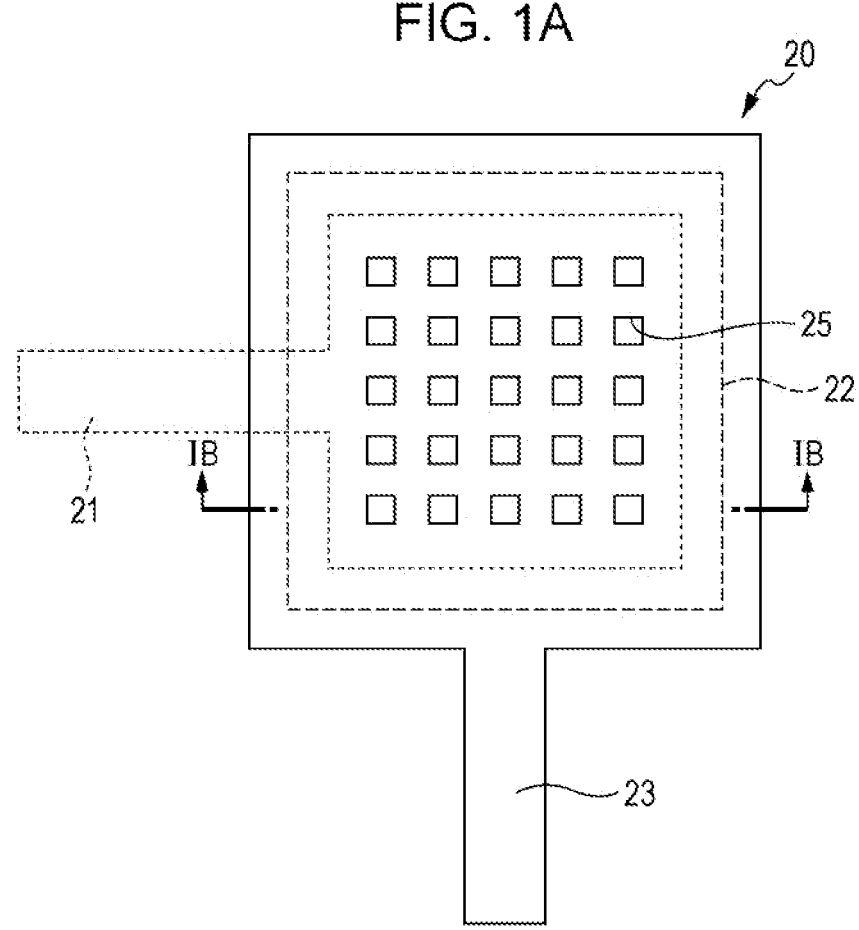
FIGS. 1A and 1B are diagrams showing a configuration example of a sensor section of a humidity detection sensor according to an embodiment of the present invention.

DESCRIPTION OF THE PREFERRED
EMBODIMENTS

The present inventors have focused on a structure in which, when a sensor section of a humidity detection sensor is configured to have a parallel-plate structure in which a humidity sensing film is interposed between upper and lower electrodes, a protective film for blocking exchange of water with the outside is provided on the upper electrode. When the structure is provided in which the humidity sensing film is interposed between the upper and lower electrodes, in order to allow water molecules to smoothly pass to the inside of the humidity sensing film, it is necessary to partially remove the protective film and the electrode formed on the humidity sensing film, thereby exposing the humidity sensing film of the sensor section to the outside. As a method for this, a method is conceivable in which an upper electrode having openings is formed on the humidity sensing film, and then a protective film is formed so as to cover the upper electrode and is partially removed by a dry etching method such as milling By so doing, it is possible to obtain a structure in which a protective film 54 is provided on an upper electrode 53 and a humidity sensing film 52 interposed between a lower electrode 51 and the upper electrode 53 is partially exposed through openings 55 (see FIG. 6). In addition, the present inventors have found that in this method, when the openings 55 formed in the protective film 54 are made smaller than openings formed in the upper electrode 53, it is possible to cover edges of the upper electrode 53 with the protective film 54 to improve the humidity resistance of the upper electrode 53.

Furthermore, as a result of further examination, the present inventors have found that there is a concern that in each opening 55 through which the humidity sensing film 52 is exposed, depending on the adhesiveness between the humidity sensing film 52 and the protective film 54 or the distance from the side surface of the upper electrode 53 to the opening 55, water molecules or a corrosion component may enter through the interface between the humidity sensing film 52 and the protective film 54 to corrode the upper electrode 53. Thus, as a result of examination in further improvement of the humidity resistance of the upper electrode, the present inventors have conceived a humidity detection sensor that, in a sensor section having a structure in which a humidity sensing film is interposed between a lower electrode and an upper electrode, smoothly supplies external water molecules to the humidity sensing film and allows the humidity resistance of the upper electrode to be more effectively improved. Hereinafter, an embodiment of the present invention will be described in detail with reference to the accompanying drawings.

Figure 3:
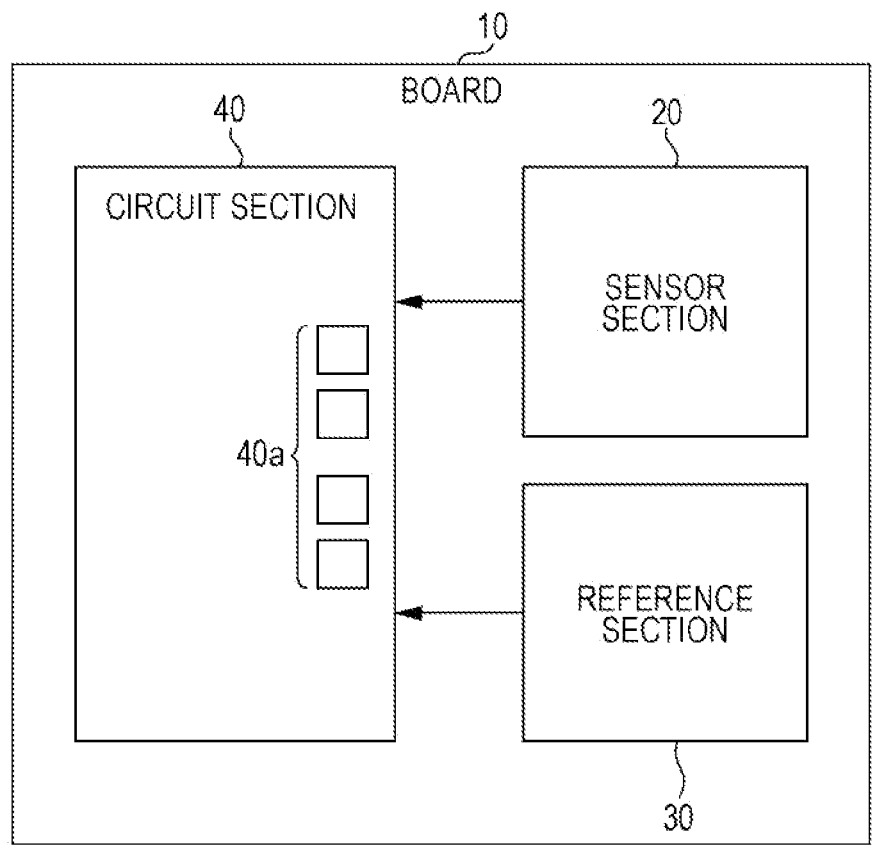
FIG. 3 is a block diagram showing the configuration of the humidity detection sensor according to the embodiment of the present invention.

FIG. 3 is a block diagram showing a configuration example of a humidity detection sensor according to the embodiment of the present invention. The humidity detection sensor shown in FIG. 3 includes, on a board 10, a sensor section 20 whose capacitance C20 changes in response to humidity, a reference section 30 which keeps its capacitance C30 constant regardless of humidity, and a circuit section 40 which is electrically connected to the sensor section 20 and the reference section 30 and which converts the capacitance difference ΔC (=C20−C30) between the sensor section 20 and the reference section 30 to a voltage and outputs the voltage to an external circuit.

The circuit section 40 is provided with a pad 40a for connection with the external circuit. In the external circuit connected to the humidity detection sensor via the pad 40a, a humidity change (relative humidity) is detected from the output of the humidity detection sensor (the voltage corresponding to the capacitance difference ΔC).

Figure 1B:
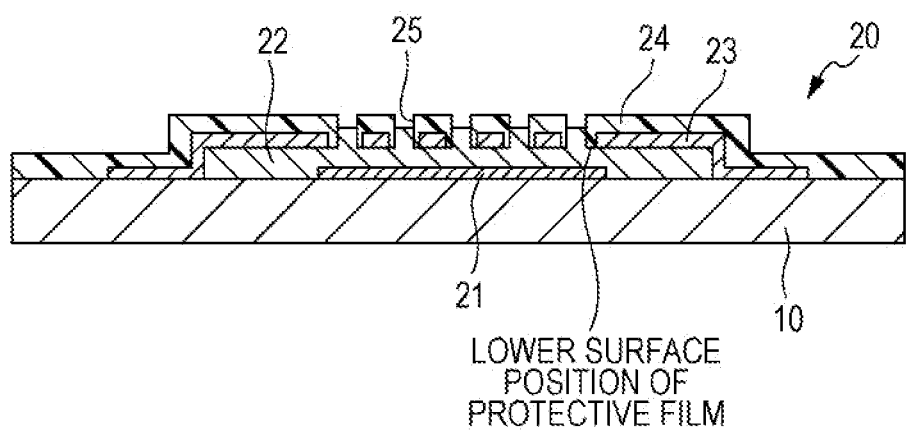

FIGS. 1A and 1B are diagrams showing the configuration of the sensor section 20 of the humidity detection sensor according to the embodiment of the present invention. FIG. 1A shows a schematic plan view of the sensor section 20, and FIG. 1B shows a schematic cross-sectional view taken along the IB-IB line in FIG. 1A. In addition, the board 10 and a protective film 24 are omitted in FIG. 1A.

The sensor section 20 has a structure in which a lower electrode 21, a humidity sensing film 22, an upper electrode 23, and the protective film 24 are laminated on the board 10, and the upper electrode 23 and the protective film 24 are provided with openings 25 through which the humidity sensing film 22 is partially exposed to the outside. In addition, the protective film 24 is formed so as to cover the upper electrode 23, and in the openings 25, the humidity sensing film 22 is provided so as to reach a position higher than the position of the lower surface of the protective film 24. Thus, it is possible to provide a configuration in which the interface at which the lower surface of the protective film 24 and the humidity sensing film 22 are in contact with each other is not exposed. It is noted that the "position" refers to a position in a direction perpendicular to the surface of the board 10.

As described above, in the parallel-plate structure in which the humidity sensing film 22 is interposed between upper and lower electrodes, when the protective film 24 is provided so as to cover the upper electrode 23 and the openings 25 are provided so as to partially expose the humidity sensing film 22 therethrough, the humidity sensing film 22 is provided also within the openings 25 so as to not expose, to the outside, the interface at which the lower surface of the protective film 24 and the humidity sensing film 22 are in contact with each other. Thus, it is possible to suppress entry of water molecules or a corrosion component through the interface. As a result, external water molecules are smoothly supplied to the humidity sensing film 22 and it is possible to effectively improve the humidity resistance of the upper electrode 23.

Figure 2A:
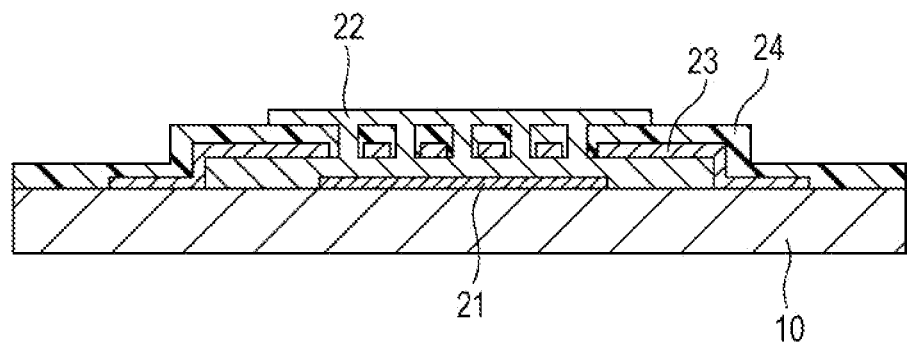
FIGS. 2A and 2B are diagrams showing another configuration example of the sensor section of the humidity detection sensor according to the embodiment of the present invention.

In addition, in light of more effectively improving the humidity resistance of the upper electrode 23, it is preferred that in the sensor section 20, the openings 25 are filled with the humidity sensing film 22 and the humidity sensing film 22 is provided also on the protective film 24 (see FIG. 2A). In this case, in a region where the openings 25 are provided, it is possible to cover the surface of the protective film 24 with the humidity sensing film 22. Thus, it is possible to effectively reduce the influence of water molecules or a corrosion component, which have entered through the interface between the protective film 24 and the humidity sensing film 22, on the upper electrode 23.

As the board 10, a board whose surface is protected by an insulator (for example, a silicon board) or the like may be used. As the materials of the lower electrode 21 and the upper electrode 23, for example, a metal thin film of Al, AlCu, Ta, Ti, NiFe, Ni, or the like may be used. As the material of the humidity sensing film 22, for example, a polymer humidity sensing film of polyimide, cellulose, PVA (polyvinyl alcohol), or the like may be used. In addition, as the protective film 24, for example, a silicon nitride (SiNx) film, a SiO2 film, an Al2O3/SiO2 laminated film, a SiO2/SiN laminated film, or the like may be used.

In the upper electrode 23 and the protective film 24, one or more openings 25 are formed so as to partially expose the humidity sensing film 22 to the outside. The openings are formed in each of the upper electrode 23 and the protective film 24, and the openings formed in the upper electrode 23 and the openings formed in the protective film 24 are provided so as to at least partially overlap each other. In addition, it is possible to arrange the openings 25 at predetermined intervals in the left-right direction and the up-down direction as shown in FIG. 1A, and the number, the planar shapes, and the formed positions of the openings 25 are arbitrary. Furthermore, in the embodiment, the shapes of the openings 25 suffice to be such shapes as to expose the humidity sensing film 22, and also include pattern shapes such as a comb shape.

Figure 2B:
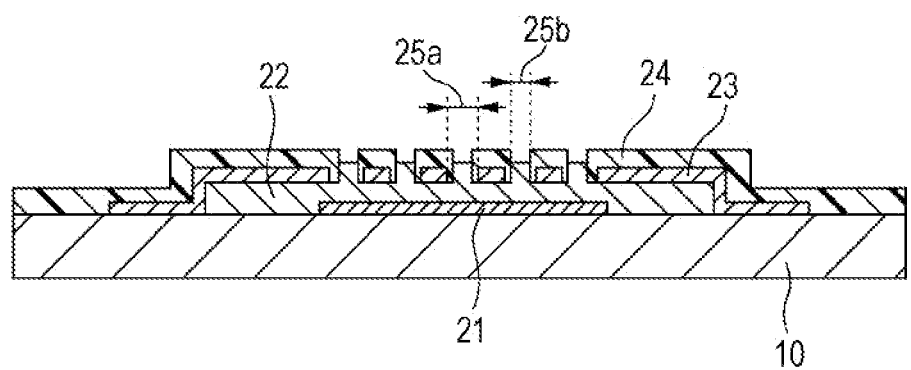

The openings 25a formed in the upper electrode 23 are made larger in size than the openings 25b formed in the protective film 24 (see FIG. 2B). Thus, even when the openings 25 are provided so as to partially expose the humidity sensing film 22, it is possible to cover edges (side surfaces) of the upper electrode 23 with the protective film 24. In this case, the sizes of the openings 25 through which the humidity sensing film 22 is exposed to the outside are the sizes of the openings 25b formed in the protective film 24.

Figure 4A:
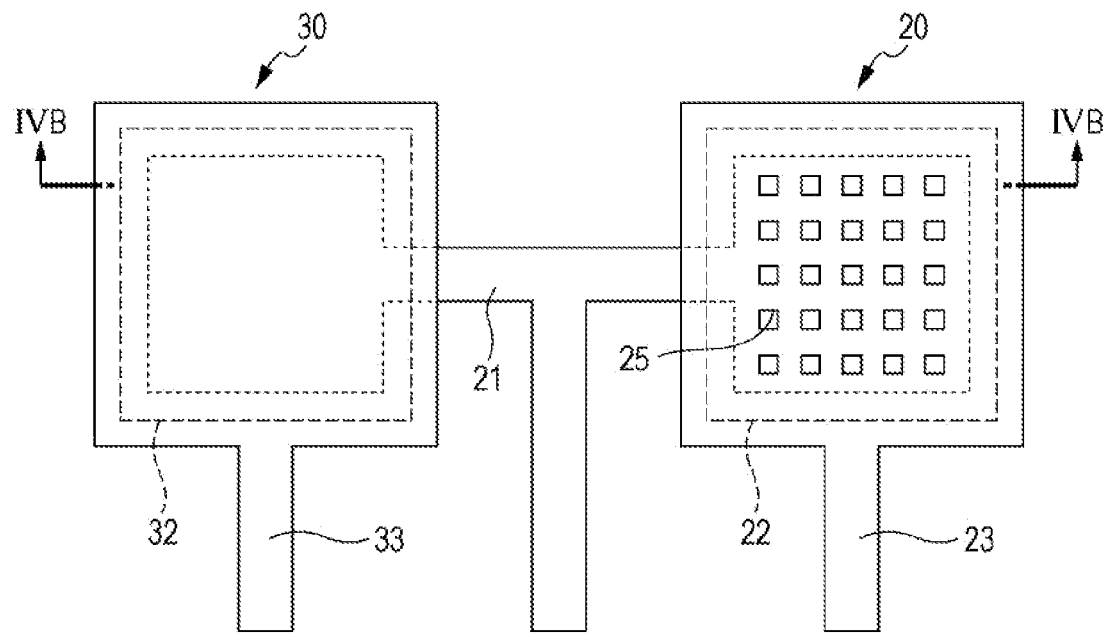
FIGS. 4A and 4B are diagrams showing a configuration example of the humidity detection sensor according to the embodiment of the present invention.
Figure 4B:
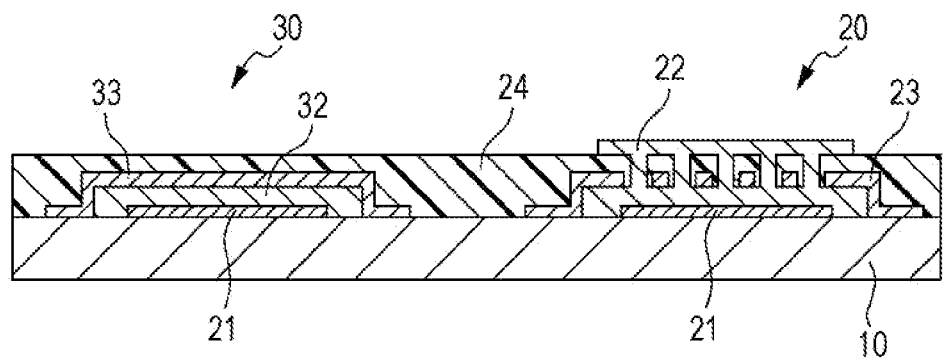

FIGS. 4A and 4B are schematic diagrams showing the sensor section 20 and the reference section 30 of the humidity detection sensor according to the embodiment of the present invention. FIG. 4A is a schematic plan view of the humidity detection sensor, and FIG. 4B is a schematic cross-sectional view taken along the IVB-IVB line in FIG. 4A. In FIGS. 4A and 4B, the sensor section 20 is located on the right side, and the reference section 30 is located on the left side. In FIG. 4A, the board 10 and the protective film 24 are omitted.

Each of the sensor section 20 and the reference section 30 has a structure in which a lower electrode, a humidity sensing film, an upper electrode, and a protective film are laminated. In other words, each of the sensor section 20 and the reference section 30 has a parallel-plate structure in which a humidity sensing film whose dielectric constant changes in response to humidity is interposed between a pair of electrodes (a lower electrode and an upper electrode).

In the sensor section 20 whose capacitance changes in response to humidity, the lower electrode 21 is formed on the board 10 via an insulating film as described above. The humidity sensing film 22 whose dielectric constant changes in response to humidity is formed on the lower electrode 21. The upper electrode 23 is partially formed on the humidity sensing film 22, and the protective film 24 for protecting the upper electrode 23 is formed. Furthermore, the openings 25 are formed in the upper electrode 23 and the protective film 24. The humidity sensing film 22 fills the openings 25 and is provided on the protective film 24 so as to be in contact with the protective film 24.

In the reference section 30 whose capacitance does not change regardless of humidity, the lower electrode 21 is formed on the board 10. On the lower electrode 21, a humidity sensing film 32 is formed so as to cover the entire lower electrode 21. On the humidity sensing film 32, an upper electrode 33 is formed so as to cover the entire humidity sensing film 32. In the entire reference section 30, a protective film 24 for protecting the upper electrode 33 is formed.

In the humidity detection sensor according to the embodiment, the lower electrode 21 may be provided so as to be shared by the sensor section 20 and the reference section 30 as shown in FIGS. 4A and 4B. In this case, a lower electrode wire is preferably led from substantially the midpoint in the lower electrode 21 between the sensor section 20 and the reference section 30 and connected to the electrode pad 40a of the circuit section 40. When the lower electrode wire is led from substantially the midpoint between the sensor section 20 and the reference section 30 as described above, electrical symmetry between the sensor section 20 and the reference section 30 is made better, and it is possible to reduce variations of the sensor capacitance C20 and the reference capacitance C30.

As the material of the upper electrode 33, the same material as that of the upper electrode 23 may be used, and for example, Al, AlCu, Ta, Ti, NiFe, Ni, or the like may be used. In addition, the upper electrode 23 and the upper electrode 33 are preferably formed simultaneously by the same process. FIGS. 4A and 4B show the case where no opening is provided in the upper electrode 33, but openings may be provided in the upper electrode 33 similarly to the upper electrode 23 of the sensor section 20.

As the material of the humidity sensing film 32, the same material as that of the humidity sensing film 22 may be used, and for example, a polymer humidity sensing film such as polyimide with which patterning is easily performed may be used.

As shown in FIGS. 4A and 4B, the humidity sensing films 22 and 23 and the upper electrodes 23 and 33 are individually provided in the sensor section 20 and the reference section 30, respectively. The upper electrodes 23 and 33 are provided with upper electrode wires, respectively, which connect the upper electrodes 23 and 33 to the electrode pad 40a of the circuit section 40. The upper electrode wires are wire patterns extending from a pair of the upper electrodes 23 and 33, respectively, with regular width dimensions, and the width dimensions are adjusted such that parasite capacitances generated in the sensor section 20 and the reference section 30 are the same. Thus, it is possible to reduce variations of the sensor capacitance C20 and the reference capacitance C30 by the parasite capacitances.

In the humidity detection sensor having the above configuration, a humidity is detected in the following manner. First, in the sensor section 20, the humidity sensing film 22 is exposed to the outside through the openings 25. Thus, in the humidity sensing film 22, the amount of absorbed or discharged water changes in response to the humidity (the amount of water) in the atmosphere, and the dielectric constant $\in$ changes. Thus, the capacitance C20 between the lower electrode 21 and the upper electrode 23 changes. Meanwhile, in the reference section 30, since the humidity sensing film 32 is not exposed to the outside, even when the humidity (the amount of water) in the atmosphere changes, the amount of water in the humidity sensing film 32 does not change, and the dielectric constant $\in$ also does not change. Thus, the capacitance C30 is kept constant between the lower electrode 21 and the upper electrode 33. Then, the capacitance difference between the capacitance C20 of the sensor section 20 and the capacitance C30 of the reference section 30 is obtained, whereby it is possible to measure the capacitance changed in response to the humidity (the difference value). The humidity detection sensor according to the embodiment is configured to convert the difference value to a voltage and output the voltage.

Next, a method for manufacturing the humidity detection sensor will be described. FIGS. 5A to 5E are cross-sectional views illustrating the method for manufacturing the humidity detection sensor according to the embodiment of the present invention.

Figure 5A:
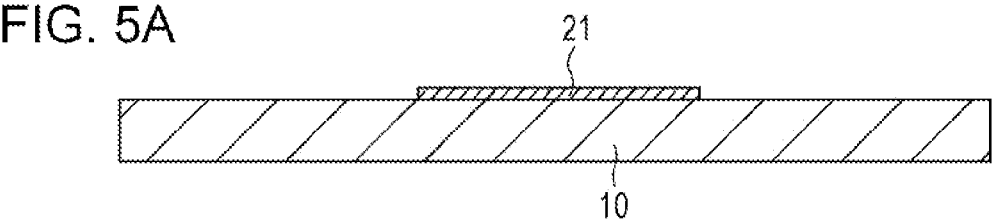
FIGS. 5A to 5E are cross-sectional views illustrating a method for manufacturing the humidity detection sensor according to the embodiment of the present invention.

First, as shown in FIG. 5A, the lower electrode 21 is formed on an insulating layer (not shown) covering the board 10. For the lower electrode 21, for example, an electrode material such as AlCu is film-formed on the entire surface of the board 10 and patterned by using a photolithography technique. Specifically, a resist layer is formed on the film-formed electrode material and then patterned as a mask, and the electrode material is etched via the mask. It is possible to share the lower electrode 21 by the sensor section 20 and the reference section 30. When forming the lower electrode 21, a wire conductor and the pad 40a of the circuit section 40 may be simultaneously formed.

Figure 5B:
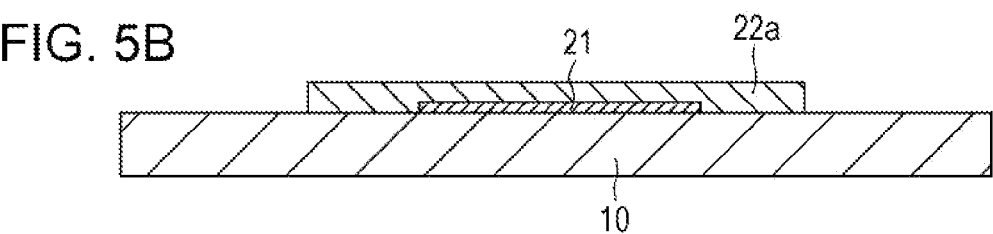

Next, as shown in FIG. 5B, on the lower electrode 21, a humidity sensing film 22a is formed so as to cover the lower electrode 21. At the same time, also on the lower electrode 21 of the reference section 30, a humidity sensing film (the humidity sensing film 32 in FIGS. 4A and 4B) is formed. For the humidity sensing film 22a, for example, a polymer material (for example, polyimide, cellulose, PVA (polyvinyl alcohol), and so on) is applied to the enter surface of the board 10 and treated with heat to be cured, and then patterned by using a photolithography technique. Specifically, a resist layer is formed on the cured polymer material and then patterned as a mask, and the polymer material is etched via the mask. The humidity sensing films are individually formed in the sensor section 20 and the reference section 30.

Figure 5C:
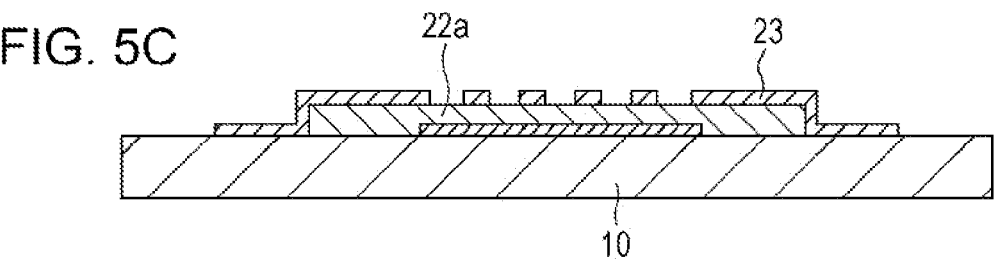

Next, as shown in FIG. 5C, on the humidity sensing film 22a, the upper electrode 23 is formed so as to cover the humidity sensing film 22a. At the same time, also on the humidity sensing film 32 of the reference section 30, an upper electrode (the upper electrode 33 in FIGS. 4A and 4B) is formed. For the upper electrode 23, for example, an electrode material such as Al, AlCu, Ta, Ti, NiFe, Ni, or the like is film-formed on the entire surface of the board 10 and patterned by using a photolithography technique. Specifically, a resist layer is formed on the film-formed electrode material and then patterned as a mask, and the electrode material is etched via the mask. In addition, at that time, openings are formed in the upper electrode 33. The upper electrodes are individually formed in the sensor section 20 and the reference section 30. The upper electrode 33 in the reference section 30 may have a structure in which no opening is provided, or may have a structure in which the same openings as those in the upper electrode 23 are provided.

Figure 5D:
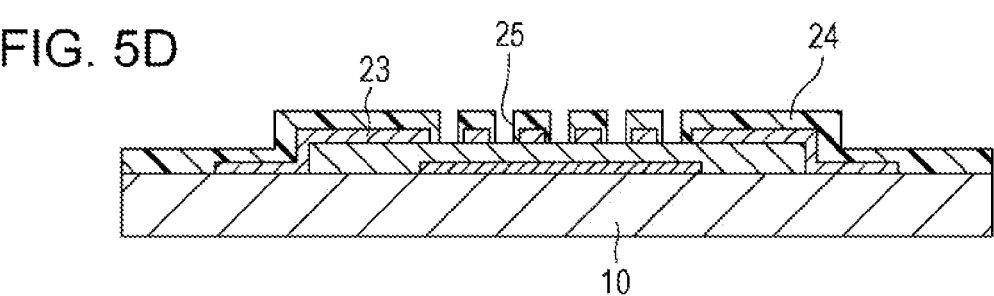

Next, as shown in FIG. 5D, on the upper electrode 23, the protective film 24 is selectively formed so as to cover the upper electrode 23. At the same time, also on the upper electrode 23 of the reference section 30, the protective film 24 is formed. For the protective film 24, for example, an insulating material such as a silicon nitride (SiNx) film, a SiO2 film, an Al2O3/SiO2 laminated film, a SiO2/SiN laminated film, or the like is film-formed on the entire surface of the board 10 and patterned by using a photolithography technique. Specifically, a resist layer is formed on the film-formed insulating material and then patterned as a mask, and the insulating material is etched via the mask. In addition, at that time, of the region of the protective film, a region that overlaps the openings of the upper electrode 23 is etched to form the openings 25. When milling is performed for forming the openings 25, it may not be possible to remove only the upper electrode 23, and the humidity sensing film 22a also may be partially removed as shown in FIG. 6. In addition, by making the openings formed in the protective film 24 smaller than the openings formed in the upper electrode 23, the edges of the upper electrode 23 are covered with the protective film 24. No opening is provided in the protective film provided on the upper electrode 33 of the reference section 30.

Figure 5E:
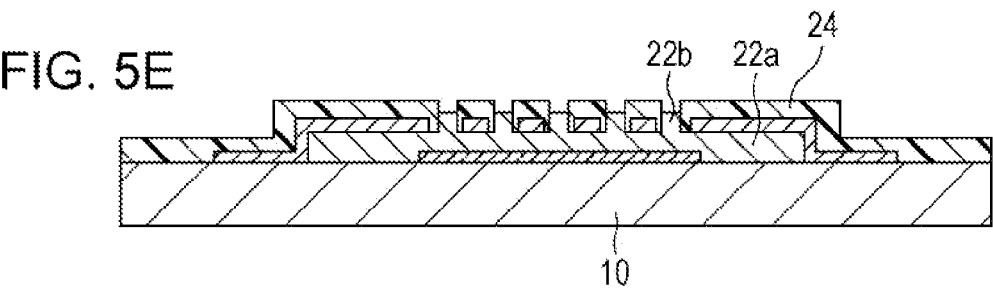

Next, as shown in FIG. 5E, the humidity sensing film 22b is formed within the openings 25. At least in the openings 25, the humidity sensing film 22b is formed so as to reach a position higher than the position of the interface at which the lower surface of the protective film 24 and the upper surface of the humidity sensing film 22a are in contact with each other. In addition, in light of reducing sensitivity variation of the humidity detection sensor, the same material as that of the humidity sensing film 22a is preferably used as the material of the humidity sensing film 22b. In this case, for example, a polymer material (for example, polyimide, cellulose, PVA (polyvinyl alcohol), and so on) is applied to the entire surface of the board 10 and treated with heat to be cured, and then patterned by using a photolithography technique. When the humidity sensing film 22a and the humidity sensing film 22b are formed from the same material, it is possible to regard the humidity sensing film 22a and the humidity sensing film 22b as a single humidity sensing film 22.

In addition, in FIG. 5E, in light of more effectively improving the humidity resistance of the upper electrode 23, it is preferred that the humidity sensing film 22b fills the openings 25 and is provided also on the protective film 24 as shown in FIG. 2A. The humidity sensing film 22b may be provided on the protective film of the reference section 30, or may not be provided thereon.

As described above, in the parallel-plate structure in which the humidity sensing film 22a is interposed between the upper and lower electrodes, even in the case where the protective film 24 is provided on the upper electrode 23 and the openings 25 are provided so as to partially expose the humidity sensing film 22a, when the humidity sensing film 22b is additionally provided such that the interface at which the lower surface of the protective film 24 and the upper surface of the humidity sensing film 22a are in contact with each other is not exposed to the outside, entry of water molecules or a corrosion component through the interface is suppressed and it is possible to effectively improve the humidity resistance of the upper electrode 23.

The present invention is not limited to the above embodiment, and modifications can be made as appropriate to practice the present invention. Although the humidity detection sensor including the sensor section and the reference section has been described in the above embodiment, the present invention is not limited thereto and is also similarly applicable to a humidity detection sensor including only a sensor section. In addition, the materials, the arranged position, the thickness, the size, and the production method of each layer, or the like in the above embodiment can be changed as appropriate to practice the present invention. Furthermore, modifications can be made as appropriate to practice the present invention without departing from the scope of the present invention.

What is claimed is:

1. A humidity detection sensor comprising:
    a board; and
    a sensor section provided on the board, a capacitance of the sensor section changing in response to humidity,
    wherein the sensor section includes:
        a lower electrode provided on the board;
        an upper electrode provided so as to face the lower electrode, the upper electrode having at least one first opening;
        a humidity sensing film formed at least between the lower electrode and the upper electrode so as to fill a space between the upper electrode and the lower electrode such that the upper electrode and the lower electrode are in contact with the humidity sensing film, a dielectric constant of the humidity sensing film changing in response to the humidity; and
        a protective film provided so as to cover the upper electrode, the protective film having at least one second opening corresponding to the at least one first opening such that the humidity sensing film is exposed therethrough, and
    wherein the humidity sensing film is provided in the second opening such that an upper surface thereof in the second opening reaches a position higher than a lower surface of the protective film in the first opening.

2. The humidity detection sensor according to claim 1, wherein the upper surface of the humidity sensing film is formed above an upper surface of the protective film such that the humidity sensing film fills the second opening and is also formed on the protective film.

3. The humidity detection sensor according to claim 1, wherein the first opening formed in the upper electrode is larger than the second opening formed in the protective film such that the protective film covers a side surface of the first opening and is in contact with the humidity sensing film in the first opening.

4. The humidity detection sensor according to claim 1, wherein the humidity sensing film is formed of one of polyimide, cellulose, and PVA.

5. The humidity detection sensor according to claim 1, further comprising:
    a reference section provided on the board, the reference section including:
        a pair of electrodes; and
        a humidity sensing film interposed between the electrodes, the humidity sensing film being formed of a same material as that of the humidity sensing film provided in the sensor section, a capacitance of the reference section not changing in response to the humidity; and
    a circuit section configured to convert a difference in the capacitance of the sensor section and that of the reference section into a voltage and to output the voltage.

6. A method for manufacturing a humidity detection sensor, comprising:
    forming a lower electrode on a board;
    forming, on the lower electrode, a first humidity sensing film whose dielectric constant changes in response to humidity;
    forming, on the first humidity sensing film, an upper electrode so as to face the lower electrode, the first humidity sensing film filling a space between the upper electrode and the second electrode such that the upper electrode and the lower electrode are in contact with the first humidity sending film;
    forming a first opening in the upper electrode so as to expose the first humidity sensing film therethrough;
    forming a protective film over the upper electrode and an exposed portion of the first humidity sensing film;
    forming a second opening in the protective film, the second opening corresponding to the first opening so as to expose the first humidity sensing film therethrough; and
    forming a second humidity sensing film in the second opening such that an upper surface of the second humidity sensing film reaches a position higher than an interface of a lower surface of the protective film and an upper surface of the first humidity sensing film in the first opening.

7. The method according to claim 6, wherein the second humidity sensing film is also formed on the protective film.

8. The method according to claim 6, wherein materials of the first humidity sensing film and the second humidity sensing film are the same.

9. The method according to claim 6, wherein the second opening is smaller than the first opening.

* * * * *